United States Patent
Ralfs et al.

(10) Patent No.: US 12,350,438 B2
(45) Date of Patent: Jul. 8, 2025

(54) VENTILATOR FOR HIGH-FLOW OXYGEN THERAPY

(71) Applicant: Drägerwerk AG & Co. KGaA, Lübeck (DE)

(72) Inventors: Frank Ralfs, Lübeck (DE); Andreas Neumann, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 988 days.

(21) Appl. No.: 17/407,001

(22) Filed: Aug. 19, 2021

(65) Prior Publication Data

US 2022/0054792 A1   Feb. 24, 2022

(30) Foreign Application Priority Data

Aug. 20, 2020   (DE) ............... 10 2020 121 871.0

(51) Int. Cl.
  *A61M 16/20*   (2006.01)
  *A61M 16/00*   (2006.01)
  *A61M 16/06*   (2006.01)

(52) U.S. Cl.
  CPC ...... *A61M 16/204* (2014.02); *A61M 16/0003* (2014.02); *A61M 16/0066* (2013.01);
  (Continued)

(58) Field of Classification Search
  CPC .. A61M 16/20; A61M 16/201; A61M 16/202; A61M 16/209; A61M 2016/003; A61M 2016/0039; A61M 2016/0042; A61M 16/0057; A61M 16/0066; A61M 16/0672; A61M 16/1005; A61M 16/101; A61M 16/024
  See application file for complete search history.

(56) References Cited

U.S. PATENT DOCUMENTS

| | | | |
|---|---|---|---|
| 5,694,926 A | | 12/1997 | Devries et al. |
| 5,954,051 A | * | 9/1999 | Heinonen ........... A61M 16/202 128/205.24 |

(Continued)

FOREIGN PATENT DOCUMENTS

| | | |
|---|---|---|
| EP | 0968735 A1 | 1/2000 |
| WO | 2009094532 A1 | 7/2009 |

(Continued)

*Primary Examiner* — Kendra D Carter
*Assistant Examiner* — Jaeick Jang
(74) *Attorney, Agent, or Firm* — McGlew and Tuttle, P.C.

(57) ABSTRACT

A ventilator (100) ventilates a patient (102) by a high-flow oxygen therapy via a tube system (104). The ventilator has at least one sensor element (110), at least one actuatable inhalation valve or exhalation valve (120) and a control unit (130). The sensor element is arranged and configured to determine and to output a measured variable (112) within the tube system. The measured variable indicates a gas flow within the tube system. The actuatable inhalation valve or exhalation valve is arranged and configured to make possible a flow of a breathing gas from a ventilation circuit (107) of the ventilator. The control unit regulates a ventilation pressure provided by the ventilator via the at least one sensor element and the at least one inhalation valve or exhalation valve such that a predefined maximum pressure is not exceeded in a predefined area (140) of the tube system.

18 Claims, 4 Drawing Sheets

(52) U.S. Cl.
CPC ...... *A61M 16/0672* (2014.02); *A61M 16/205* (2014.02); *A61M 2016/0027* (2013.01); *A61M 2016/0036* (2013.01); *A61M 2202/0208* (2013.01); *A61M 2205/70* (2013.01)

(56) References Cited

U.S. PATENT DOCUMENTS

| | | |
|---|---|---|
| 2011/0125052 A1 | 5/2011 | Davenport et al. |
| 2013/0263854 A1* | 10/2013 | Taylor ............... A61M 16/0066 128/204.23 |
| 2019/0111226 A1* | 4/2019 | Holley ............... A61M 16/024 |
| 2021/0052839 A1* | 2/2021 | Li ......................... A61M 16/06 |

FOREIGN PATENT DOCUMENTS

| | | |
|---|---|---|
| WO | 2015155342 A1 | 10/2015 |
| WO | 2020043671 A1 | 3/2020 |

\* cited by examiner

VENTILATOR FOR HIGH-FLOW OXYGEN THERAPY

CROSS REFERENCE TO RELATED APPLICATIONS

This application claims the benefit of priority under 35 U.S.C. § 119 of German Application 10 2020 121 871.0, filed Aug. 20, 2020, the entire contents of which are incorporated herein by reference.

TECHNICAL FIELD

The present invention pertains to a ventilator for ventilating a patient by a high-flow oxygen therapy via a tube system. The present invention pertains, furthermore, to a ventilation system for ventilating a patient by a high-flow oxygen therapy, to a process for regulating a ventilation pressure provided by a ventilator and to a computer program with a program code for carrying out such a process.

TECHNICAL BACKGROUND

An oxygen concentration and a gas flow are typically set at a corresponding ventilator in high-flow oxygen therapy. This gas flow is then sent via a patient interface to a patient to be ventilated. The gas flow takes place in this case via a tube system, which comprises at least one tube. One-tube systems and two-tube systems with a Y-piece located between them are known, in principle, for high-flow oxygen therapy. The patient interface in this case ensures a ventilation by means of a dynamic overpressure, as it can be provided, for example, by so-called prongs (nasal prongs). The gas flow flows here for the most part past the patient and into the surrounding area. The patient interface does not seal the airways of the patient, and the degree of the corresponding leakage between the patient to be ventilated and the patient interface determines the pressure provided within the airways of the patient. At the same time, a possible dead space is rinsed by turbulence of the gas.

The use of a spring-loaded valve, via which it is ensured that the corresponding excess gas is released via the spring-loaded valve when a pressure limit is reached in the tube system, is known for such a ventilation.

SUMMARY

An object of the present invention is to provide an improved ventilator, particularly an especially reliable ventilator for a high-flow oxygen therapy.

A ventilator for ventilating a patient by a high-flow oxygen therapy via a tube system is proposed according to the present invention for accomplishing this object, wherein the ventilator has especially a sensor device comprising at least one sensor element, an actuatable valve configuration comprising at least one of an actuatable inhalation valve or an actuatable exhalation valve and a control unit.

The at least one sensor element is arranged and configured to determine and to output a measured variable within the tube system, wherein the measured variable indicates a gas flow within the tube system.

The at least one actuatable inhalation valve and/or exhalation valve (the actuatable valve configuration), especially the at least one electrically actuatable inhalation valve or exhalation valve, is arranged and configured to make possible a flow of a breathing gas from the ventilation circuit of the ventilator.

The control unit regulates a ventilation pressure provided by the ventilator via the at least one sensor element and the at least one inhalation valve or exhalation valve such that a predefined maximum pressure is not exceeded in a predefined area of the tube system.

It was found within the framework of the present invention that high pressures directly at the patient must be avoided in order to ensure the patient's health. The use of an actuatable inhalation valve or exhalation valve, via which a simultaneously high gas flow is ensured during the high-flow oxygen therapy over the entire duration of the therapy, taking into consideration the predefined maximum pressure, is proposed for this.

Due to the possibility of actuating the inhalation valve or exhalation valve, a pressure level that is hazardous for the patient to be ventilated can be avoided in an automated manner during the ventilation without it being necessary to change the gas flow provided. The desired high-flow oxygen therapy can thus be carried out over the complete desired duration of the therapy, without the risk of an excessively high pressure occurring at the patient.

The sensor device comprises at least one sensor element that comprises at least one sensor mechanism part and a connection part, which connects the sensor mechanism part directly or indirectly to the control unit. The at least one sensor element is preferably a sensor, for example, a pressure sensor or a flow sensor. The specific configuration of such sensors (sensor device) is known and will not therefore be explained below.

An inhalation valve is a valve through which a gas flow provided for inhalation by the patient can escape. An exhalation valve is a valve through which an exhaled gas of the patient can escape. An inhalation valve is preferably arranged in the area of an inhalation tube and an exhalation valve is arranged in the area of an exhalation tube.

The control unit preferably comprises one or more processor and a memory module, in which the predefined maximum pressure is stored. The control unit accesses this stored, predefined maximum pressure during the regulation of the ventilation pressure and the control unit compares this to a value that is indicated by the outputted measured variable. The predefined maximum pressure is a value here that indicates a maximum pressure that is present. In one embodiment, the maximum pressure is a variable from which the pressure occurring maximally in the predefined area of the tube system can be directly determined.

The components of the ventilator according to the present invention may be arranged in a common housing or at least partially at spaced locations from one another. The tube system is not a part of the ventilator according to the present invention in this case.

The ventilation circuit may be open in the sense of the present invention, for example, for a one-tube structure of the tube system, or it may be closed, as in the case in which, for example, an inhalation tube and an exhalation tube are provided.

Preferred embodiments of the ventilator according to the present invention will be described below.

In an especially preferred embodiment, the ventilator is configured to hold the at least one inhalation valve or exhalation valve closed if the predefined maximum pressure is not reached in the predefined area of the tube system. The inhalation valve or exhalation valve does not influence in this embodiment the gas flow during the high-flow oxygen therapy as long as no critical pressure is present in the predefined area.

The at least one sensor element is preferably arranged within an exhalation tube. A measured variable, which indicates a quantity of gas flowing past a patient interface per unit of time, is determined in this embodiment. It can thus be determined by the sensor element whether an unusually large quantity of gas is collecting right now in the area of the exhalation tube, which may be, for example, evidence of a patient interface being tightly in contact with the patient. Without leakage, the gas flow typically leads within the framework of the high-flow oxygen therapy to an excessively high gas pressure acting on the patient. Due to an excessively low leakage being detected, it can be decided especially reliably by the control unit that the corresponding inhalation valve or exhalation valve must be actuated such that the pressure preset at the patient is reduced. The gas flow is not reduced in the process at the patient according to the present invention.

In a preferred embodiment, the control unit carries out the regulation of the ventilation pressure provided without changing for this purpose the output of a blower of the ventilator or the like. As a result, a constant gas flow is ensured at the patient, as it is necessary for the high-flow oxygen therapy. The regulation by the control unit preferably takes place here exclusively by the opening of the corresponding inhalation valve or exhalation valve in the presence of a pressure within the predefined area of the tube system, which pressure exceeds the predefined maximum pressure.

The inhalation valve or exhalation valve is preferably an electrically actuatable inhalation valve or electrically actuatable exhalation valve (the actuatable valve configuration comprises at least one of an electrically actuatable inhalation valve or an electrically actuatable exhalation valve). As a result, the regulation by the control unit can take place especially reliably and rapidly. In an alternative or additional exemplary embodiment, the actuatable valve configuration comprising the inhalation valve or the exhalation valve can be actuated mechanically pneumatically or in another manner by the control unit.

The sensor device comprising at least one sensor element is especially preferably a pressure sensor and/or a flow sensor. Such a sensor element can indicate the pressure present directly, without time-consuming algorithms for signal processing, and/or it can indicate the pressure present on the basis of a defined gas flow.

The at least one sensor element is preferably arranged in the predefined area of the tube system. As a result, it can be directly determined from the determined sensor data whether the predefined maximum pressure is exceeded or not. In an alternative or additional embodiment, the at least one sensor element is arranged at a spaced location from the predefined area of the tube system. The measured variable determined must be converted in this embodiment into a value that indicates the pressure ion the predefined area of the tube system.

In an especially preferred embodiment, the control unit is configured, furthermore, to regulate the ventilation pressure provided on the basis of predefined calibration information. The predefined calibration information is preferably stored in a memory module of the control unit. Based on the predefined calibration information, the pressure within the predefined area of the tube system can be inferred from the determined measured variable especially reliably.

In an especially advantageous variant of the preceding embodiment, the calibration information indicates a relationship between the pressure present in the predefined area of the tube system and the gas flow measured by the at least one flow sensor. Such a relationship can be obtained by a functional assignment, by a graphic assignment based on a diagram and/or on the basis of a predefined assignment of value pairs. The calibration information preferably takes into consideration here geometric properties of the tube system. In a preferred embodiment, calibration information is determined within the framework of a test operation of the ventilator before a subsequent use of the ventilator at the patient to be ventilated.

In an especially advantageous variant of the above embodiment, the calibration information is based, furthermore, on a tube resistance, especially a predefined tube resistance, of the tube system. The geometry of at least one part of the tube system is taken into consideration in this variant in the determination of the calibration information. As a result, the pressure present in the predefined area can be inferred hereby especially advantageously from the measured variable, for example, from a gas flow or from a pressure. The measured variable is determined now especially preferably in the predefined area. For example, the pressure indicated by the gas flow within the tube area in question can be inferred directly on the basis of the tube resistance via a measured gas flow.

The predefined area of the tube system is especially preferably an end of an inhalation tube or exhalation tube, which end points towards the patient. An excessively high pressure at the patient can be avoided in this embodiment especially reliably because the predefined maximum pressure is not exceeded according to the present invention directly in the area of the patient, namely, at a corresponding end of the inhalation tube or exhalation tube. Should this predefined maximum pressure be exceeded in this area at the patient, the inhalation valve or exhalation valve is opened by the control unit and the pressure is reduced for protecting the patient.

In an advantageous embodiment, the at least one inhalation valve or exhalation valve is arranged together with the control unit in a housing of the ventilator. The ventilator according to the present invention can advantageously be used in this embodiment for different tube systems, without the manner of functioning of the inhalation valve or exhalation valve being compromised thereby. The inhalation valve or exhalation valve is preferably arranged now in the area of a gas feed to the tube system, or of a gas return from the tube system.

In an advantageous embodiment, the at least one inhalation valve or exhalation valve may be only in an open valve position and in a closed valve position and the inhalation valve or exhalation valve has an especially simple configuration in this embodiment. As a result, this valve can be especially robust and can be manufactured in a favorable manner. Such a valve with only two different valve positions may have an especially high level of failure safety, which is advantageous for the reliability of the ventilator according to the present invention.

The predefined maximum pressure can preferably be set individually. The predefined maximum pressure is preferably between 5 mbar and 25 mbar, especially between 10 mbar and 20 mbar, and especially preferably about 12 mbar. The predefined maximum pressure can especially preferably be set individually between 5 mbar and 25 mbar, especially between 10 mbar and 20 mbar.

Further, the ventilator is preferably configured to display via a display unit when an actuation of the inhalation valve or exhalation valve has been brought about by the control unit. As a result, a user is informed that the predefined maximum pressure was exceeded in the predefined area of the tube system. This may indicate, for example, that a desired leakage is not present at an interface of the tube system to the patient.

According to a second aspect of the present invention, a ventilation system for ventilating a patient by a high-flow oxygen therapy with a ventilator according to the present invention according to at least one of the above embodiments and with a tube system with an inhalation tube and with an exhalation tube is proposed for accomplishing the above-mentioned object, wherein the tube system is connected to the ventilator for providing a ventilation circuit.

The ventilation system according to the present invention comprises the ventilator according to the present invention and hence also all the advantages of this ventilator.

Furthermore, the tube system may be adapted in terms of its geometry to the ventilator, so that the control device can regulate the inhalation valve or exhalation valve especially reliably for the tube geometry actually present.

The at least one sensor element is preferably arranged within the tube system and is connected for signal technology to the control unit of the ventilator.

The inhalation valve or exhalation valve is preferably arranged in the tube system in order to make possible a flow of the breathing gas from the ventilation circuit of the ventilator directly at the tube system.

In an advantageous embodiment, a connection of the tube system to the patient is provided by means of prongs (nasal prongs). Such a connection via prongs can be changed during the use of these prongs in terms of the leakage provided in the process, so that the ventilator according to the present invention is especially advantageous for the use of such prongs. The predefined maximum pressure can thus also be avoided in case of a leakage that varies over time.

According to a third aspect of the present invention, a process for regulating a ventilation pressure provided by a ventilator during a high-flow oxygen therapy via a tube system is proposed for accomplishing the above-mentioned object. The process according to the present invention has the following steps:
  Provision of at least one actuatable inhalation valve or exhalation valve, especially of an electrically actuatable inhalation valve or exhalation valve, for making possible a flow of a breathing gas from a ventilation circuit of the ventilator,
  determination and outputting of a measured variable within the tube system, wherein the measured variable indicates a gas flow within the tube system, and
  regulation of a ventilation pressure provided by the ventilator via the at least one inhalation valve or exhalation valve such that a predefined maximum pressure is not exceeded in a predefined area of the tube system.

The process according to the third aspect of the present invention is carried out by the ventilator according to the first aspect of the present invention, so that it comprises the advantages of the ventilator. The process makes possible, in particular, a constantly present gas flow at the patient during the high-flow oxygen therapy while the risk of an excessively high gas pressure at the patient is avoided at the same time.

According to the fourth aspect of the present invention, a computer program with a program code for carrying out a process according to the third aspect of the present invention when the program code is executed on a computer, on a processor or on a programmable hardware component is proposed for accomplishing the above-mentioned object. A plurality of steps of the process according to the present invention are preferably carried out by a shared computer, by a shared processor or by a shared programmable hardware component. The individual steps are preferably separated here from one another at the software level by corresponding software blocks. All steps of the process according to the present invention are especially preferably carried out on a shared computer, on a shared processor or on a shared programmable hardware component.

The present invention shall be explained now in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
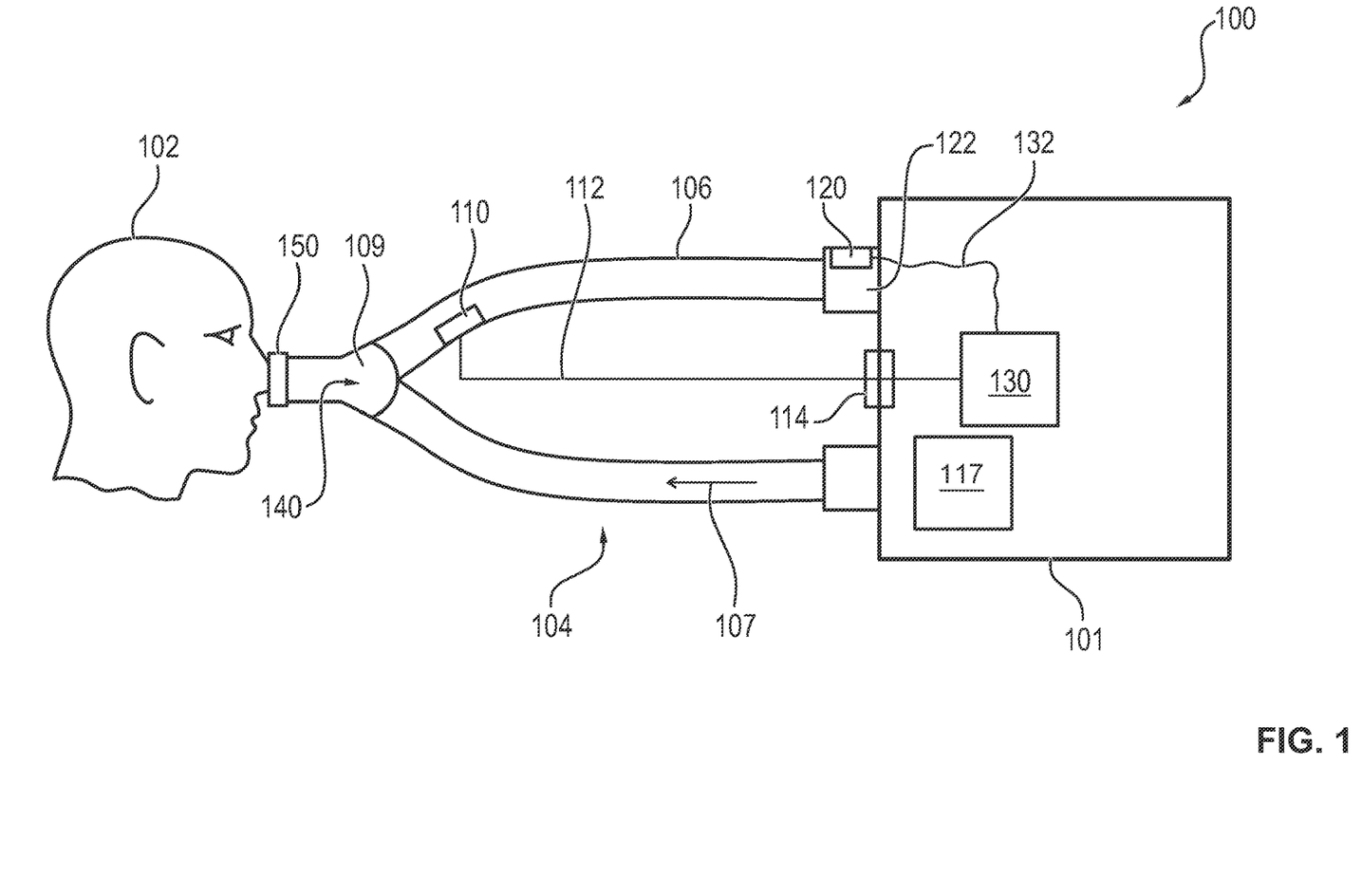
FIG. 1 is a schematic view of a first exemplary embodiment of a ventilator according to a first aspect of the present invention.

Referring to the drawings, FIG. 1 shows a schematic view of a first exemplary embodiment of a ventilator 100 according to a first aspect of the present invention.

The ventilator 100 according to the present invention is configured for ventilating a patient 102 by a high-flow oxygen therapy via a tube system 104.

The ventilator 100 comprises a sensor device, which comprises at least one sensor element 110, an actuatable valve configuration, which comprises at least one of an actuatable inhalation valve or exhalation valve 120, and a control unit 130.

The at least one sensor element 110 in the exemplary embodiment shown is a flow sensor, which is arranged and configured to determine and to output a measured variable, namely, a gas flow in the area of the sensor element 110 in this case, within the tube system 104. The flow sensor is arranged for this purpose in an exhalation tube 106 of the tube system 104 at an end of this exhalation tube 106, which end points towards (is directed towards or is adjacent to) the patient 102. The flow sensor is connected to the control unit 130 in a cable-based manner (cable connected) in this case. In one exemplary embodiment, not shown, the at least one sensor element is connected to the control unit in a wireless manner (wirelessly connected). In another exemplary embodiment, not shown, the sensor element is connected to the control unit indirectly via an additional processing unit of the ventilator.

The connection between the control unit 130 and the sensor element 110 is established via an interface 114 at the housing 101 of the ventilator 100. The data provided, which indicate the measured variable 112, are provided via this interface 114 via a signal that can be read by the control unit 130.

The actuatable valve configuration, comprising at least one actuatable inhalation valve or exhalation valve 120, is arranged and configured to make possible a flow of a breathing gas from a ventilation circuit 107 of the ventilator 100. This particularly provides for a controlled venting of the ventilation circuit 107, namely a flow of the breathing gas provided by the respective valve of the valve configuration as a flow out of the ventilation circuit 107. In one exemplary embodiment shown, the actuatable valve configuration is an exhalation valve, which is formed for the exhalation tube 106 in the area of a mount 122 of the ventilator 100. No structural change of the tube system is necessary as a result for transposing the valve 120 according to the present invention. In an alternative or additional exemplary embodiment, not shown, the valve (actuatable valve configuration) according to the present invention is an inhalation valve, which is formed in a mount of the ventilator for an inhalation tube. The exhalation valve 120 in the exemplary embodiment shown is actuated by the control unit 130 such that it remains closed as long as the predefined maximum pressure is not reached in the predefined area 140 of the tube system 104. It is only after such a predefined maximum pressure is indicated via the at least one sensor element 110 that the exhalation valve 120 is opened and a gas flow out of the ventilation circuit 107 is made possible thereby.

The control unit 130 is connected to the sensor element 110 via the interface 114 and is connected directly to the exhalation valve 120 via a corresponding valve cable 132. In one exemplary embodiment, not shown, the control unit is connected to the inhalation valve or exhalation valve in a wireless manner. In the exemplary embodiment shown, the connection via the valve cable 132 makes possible an electrical control, via which a valve position of the exhalation valve 120 can be changed electrically. In one exemplary embodiment, not shown, the inhalation valve or exhalation valve is actuated by the control unit via a pneumatic actuating device and/or via a mechanical actuating device. The control unit 130 is configured to regulate a ventilation pressure provided by the ventilator 100 within the ventilation circuit 107 via the at least one sensor element 110 and via at least one inhalation valve or exhalation valve 120 such that a predefined maximum pressure in the predefined area 140 of the tube system 104 is not exceeded. The predefined area 140 is an area at the Y-piece 109 of the tube system 104 in this case. Due to the sensor element 110 being arranged close to the Y-piece 109 of the tube system, the gas pressure in the area of the Y-piece 109 can be inferred from the outputted measured variable.

The predefined maximum pressure in the exemplary embodiment shown is between 5 mbar and 25 mbar, especially between 10 mbar and 20 mbar and especially preferably about 12 mbar.

The tube system 104 is connected to the patient 102 via a patient interface 150 in the exemplary embodiment shown. The patient interface 150 is only a connection to a nose area of the patient 102. This is a connection that allows a leakage between the tube system 104 and the patient 102. In one exemplary embodiment, not shown, the patient interface is a connection to the nose area and to a mouth area of the patient. The patient interface 150 is preferably represented by so-called prongs (nasal prongs), which are inserted into a respective nostril each of the patient and thus they introduce the gas to be used for the ventilation of the patient 102 directly into the airways of the patient 102.

The ventilation circuit 107 is preferably provided via a blower or similar device 117, of the ventilator 100. The output of the blower or of a similar device 117 providing a gas flow is not changed by the control unit 130 in the presence of the predefined maximum pressure in the predefined area 140 in the exemplary embodiment shown. The regulation by the control unit 130 is based in this case exclusively on the control of the actuatable valve configuration, namely at least one of the inhalation valve or exhalation valve 120.

The control unit 130 is arranged within the housing 101 of the ventilator 100. The inhalation valve or exhalation valve 120 is arranged within the mount 122 and hence likewise at the housing 101. The sensor element 110 is arranged at the tube system 104 and hence outside of the housing 101. In one exemplary embodiment, not shown, the sensor element is likewise arranged within and/or at the housing of the ventilator according to the present invention. A greater distance between the sensor element and the predefined area of the tube system than in the exemplary embodiment shown makes it necessary to convert the determined measured variable into a measured variable foreseeably occurring in the predefined area by a corresponding conversion.

The inhalation or exhalation valve 120 in the exemplary embodiment shown has an electrically actuatable flap, which is either in an open state or in a closed state, depending on the actuation by the control unit 130. The exhalation valve present in this case can correspondingly be switched via the electrical actuation by the control unit 130 between the corresponding open valve position and the corresponding closed valve position. In an alternative or additional exemplary embodiment, the corresponding valve is configured such that it can provide a plurality of different flow resistances within the framework of a plurality of valve positions. The specific configuration of such a valve is known to the person skilled in the art and it will not therefore be explained below in detail.

Figure 2:
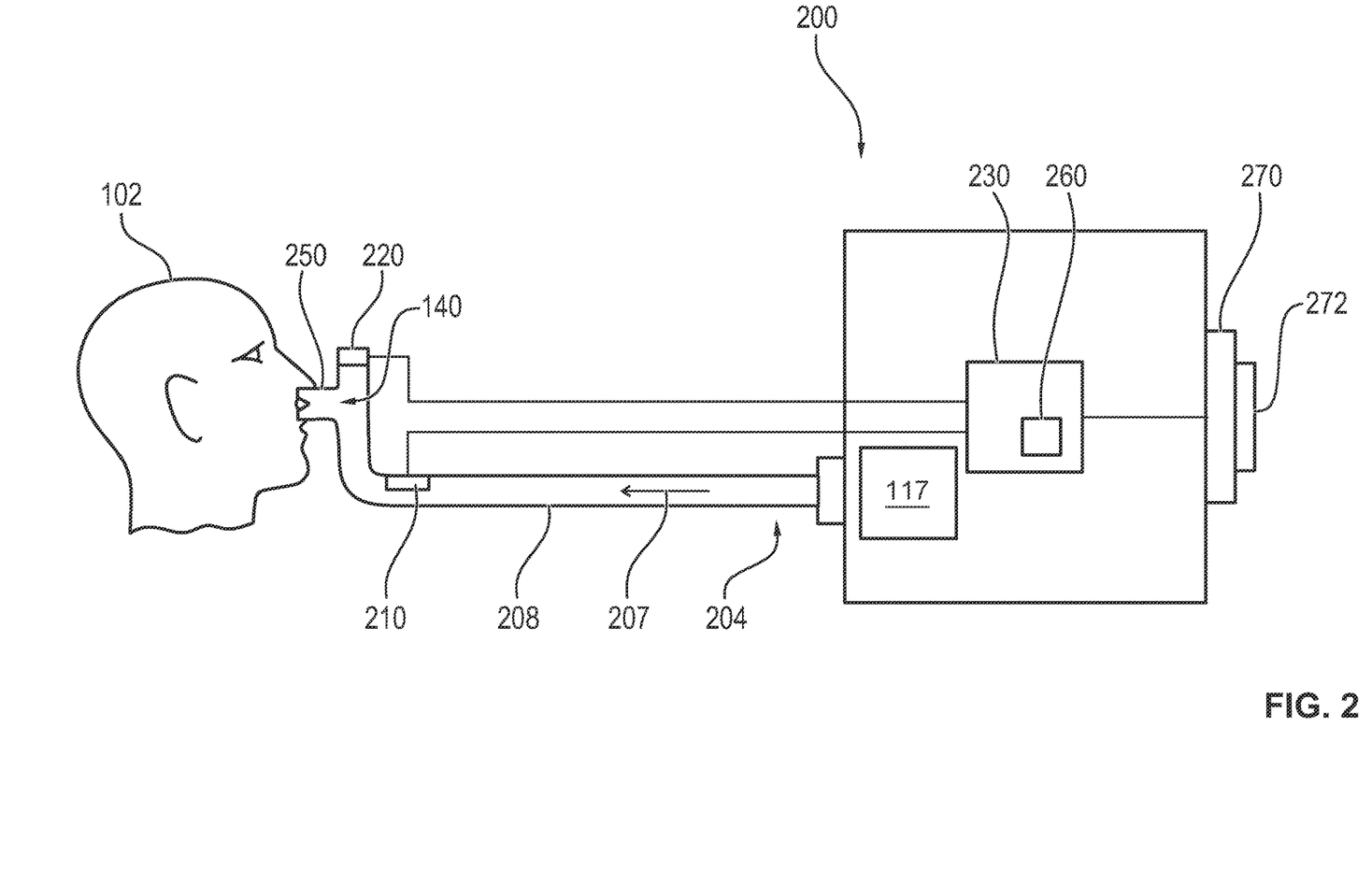
FIG. 2 is a schematic view of a second exemplary embodiment of a ventilator according to the first aspect pf the present invention.

FIG. 2 shows a schematic view of a second exemplary embodiment of a ventilator 200 according to the first aspect of the present invention.

The ventilator 200 differs from the ventilator 100 shown in FIG. 1 in that the tube system 204 comprises only an inhalation tube 208 and the corresponding patient interface 250 with the patient 102. The complete breathing gas flow 207 provided shall therefore be sent to the patient 102 in this case via the patient interface 250, which provides a connection to the nose of the patient 102 here through prongs. The breathing gas flow 207 forms a ventilating circuit for the shown structure of the tube system 204 in this exemplary embodiment. If a leakage between the patient interface 205 and the patient 102 is too small and the gas pressure acting on the patient therefore exceeds a harmless extent, the sensor device, comprising at least one sensor element 210, which is a pressure sensor in this case, detects such an increase in the gas pressure. If the predefined maximum pressure in the predefined area 140, namely, in the area of the patient interface 250 in this case, is exceeded now or will foreseeably be exceeded, the actuatable valve configuration, in this case the inhalation valve 220, which is formed at an extension of the inhalation tube 208, will open. The inhalation valve 220, just like the exhalation valve from FIG. 1, has a flap, which can switch only between an open position and a closed position depending on an electrical actuation.

The breathing gas flow 207 provided is selected during the normal operation of the ventilator 200 such that the total amount of breathing gas provided is discharged at the patient interface 250. A part of the breathing gas is sent into the nose of the patient 102 in this case and the rest is caused to pass by this patient based on a leakage between the patient interface 250 and the patient 102. It is only when the prongs of the patient interface 250 are too close to the nose and the leakage is correspondingly too small that the pressure increases within the tube system 204 and can lead to a pressure harmful for the health of the patient 102 above the predefined maximum pressure without a corresponding regulation of the control unit 230.

Calibration information 260 is permanently stored in the control unit 230. The control unit regulates the corresponding valve 220 depending on the calibration information 260. The calibration information represents an assignment between the pressure measured by the pressure sensor 210 and the pressure present in the predefined area 140. The calibration information 260 is stored here in a memory module of the control unit 230, wherein the memory module is not shown.

The ventilator 200 comprises, furthermore, an output unit 270, which indicates via a display 272 whether an actuation of the inhalation valve or exhalation valve 220 has taken place in order to avoid the maximum pressure in the predefined area 140. As a result, a user of the ventilator 200, e.g., medical professional staff, can detect that the tube system 204 may not currently be loosely in contact, as desired, with the patient 102 via the patient interface 250. An action taken by the medical professional staff to regulate the pressure within the tube system 204 can be triggered in this sense directly via the output unit 270.

Figure 3:
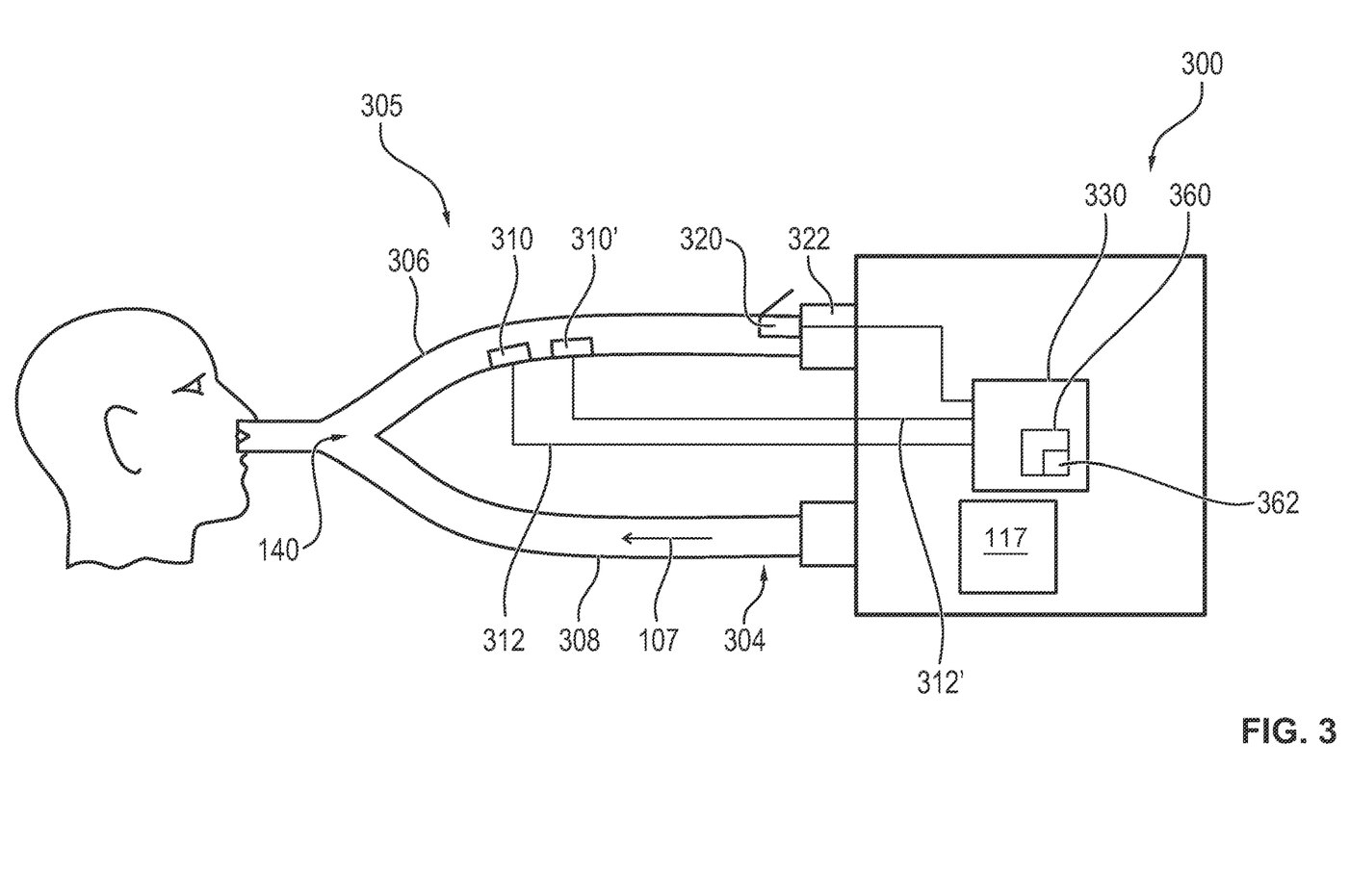
FIG. 3 is a schematic view of an exemplary embodiment of a ventilation system according to a second aspect of the present invention.

FIG. 3 shows a schematic view of an exemplary embodiment of a ventilation system 305 according to a second aspect of the present invention.

The ventilation system 305 comprises a ventilator 300 according to the first aspect of the present invention and the tube system 304. The tube system 304 is connected here to the ventilator 300 for providing the ventilation circuit 107. The tube system 304 has the same structure here as the tube system 104 from FIG. 1 and it accordingly has an exhalation tube 306 and an inhalation tube 308.

Unlike the ventilator 100 from FIG. 1, the ventilator 300 has a sensor device comprising two sensor elements 310, 310', both of which are arranged at the exhalation tube 306. The sensor elements are represented by a flow sensor and by a pressure sensor. Due to the combination of the two determined measured variables 312, 312', it can be determined by the control unit 330 in an especially reliable manner whether the inhalation valve or exhalation valve 320 must be actuated in order to avoid the predefined maximum pressure in the predefined area 140.

The control unit 330 accesses for this stored calibration information 360, which comprises a tube resistance 362, especially a predefined tube resistance, of the tube system 304 in the exemplary embodiment being shown. It is preferably detected by the ventilator automatically which tube system 304 is connected to the ventilator, and the corresponding calibration information, which provides a reliable association of measured gas flow and of measured gas pressure with the gas pressure present in the predefined area 104, and which is associated with the stored, predefined tube resistance of the detected tube system 304, is used as a function of the stored, predefined tube resistance of the detected tube system 304. The automated detection of the tube system 304 present is carried out, for example, by reading an identification number in the area of a mount 322 of a respective tube by the ventilator 300. The use of two sensors for the ventilator according to the present invention can increase a failure safety against the failure of a sensor. The two determined measured variables can thus, for example, be compared to one another in order to detect an error in the determination of a measured variable and to output a corresponding error signal.

An exhalation valve 320 as the actuatable valve configuration, which is arranged at the end of the exhalation tube 306, which end points to the ventilator 300, is used as the valve in this case. The valve is shown in FIG. 3 in an opened state, i.e., with the flap opened. Consequently, the predefined maximum pressure was reached in the predefined area 140 in the state shown or it was detected that this maximum pressure will probably be reached during unchanged operation, so that a gas flow will be released from the tube system 304 in an environment of the ventilator 300.

According to the present invention, all positions at the respective tube system being used or within a gas duct in the housing of the ventilator according to the present invention are possible for the position of the respective, at least one sensor element and of the at least one actuatable inhalation valve or exhalation valve. Thus, it must be possible to infer only the pressure present in the predefined area on the basis of the measured variable, which is also possible in case of a certain distance in space from the predefined area in case of a corresponding calibration. The corresponding valve must only have a pneumatic connection to the predefined area of the tube system in order to make possible a regulation of the pressure present there. This is also possible, for example, for a valve within the housing of the ventilator.

The communication between the sensor elements 310, 310' and the control unit 330, as well as between the exhalation valve 320 and the control unit 330 takes place in a cable-based manner in the exemplary embodiment shown. The communication takes place at least partially in a wireless manner in one exemplary embodiment, not shown.

Figure 4:
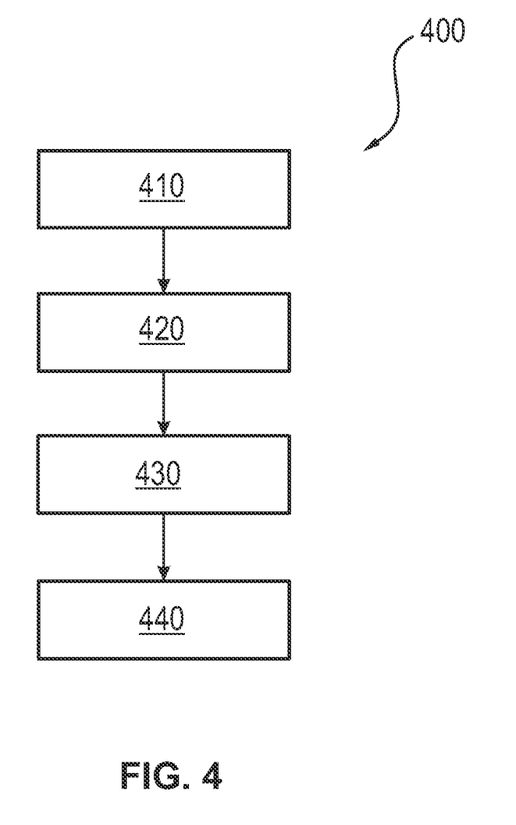
FIG. 4 is a flow chart of an exemplary embodiment of a process according to a third aspect of the present invention.

FIG. 4 shows a flow chart of an exemplary embodiment of a process 400 according to a third aspect of the present invention.

The process 400 according to the present invention is configured for the regulation of a ventilation pressure provided by a ventilator during a high-flow oxygen therapy via a tube system. It has the steps described below for this purpose.

A first step 410 comprises the provision of at least one actuatable inhalation or exhalation valve, especially of an electrically actuatable inhalation or exhalation valve, for making possible a flow of a breathing gas from a ventilation circuit of the ventilator.

A next step 420 comprises a determination of a measured variable within the tube system, wherein the measured variable indicates a gas flow within the tube system.

A step 430 directly following step 420 comprises an outputting of this measured variable.

A final step 440 comprises a regulation of a ventilation pressure provided by the ventilator via the at least one inhalation valve or exhalation valve such that a predefined maximum pressure is not exceeded in a predefined area of the tube system.

The first step 410 is carried out typically during the manufacture of the ventilator and/or of a system comprising a ventilator and a tube system. Only steps 420, 430 and 440 follow after the manufacture of this ventilator or of this system.

Steps 420 and 430, i.e., the determination and outputting of the measured variable, are preferably carried out immediately one after another. The time offset between these two steps is preferably shorter than 20 sec., especially shorter than 10 sec. and preferably shorter than 5 sec.

The two steps 420 and 430 are preferably carried out independently from step 440 at recurring time intervals. The measured variable is preferably determined again and outputted after less than 1 min., especially after less than 30 sec., and especially preferably after less than 5 sec.

The final step 440 is preferably carried out only if the outputted measured value indicates that the predefined maximum pressure is exceeded or will foreseeably be exceeded. If the predefined maximum pressure will not foreseeably be reached in view of the determined measured variable, no regulation is preferably carried out corresponding to step 440.

While specific embodiments of the invention have been shown and described in detail to illustrate the application of the principles of the invention, it will be understood that the invention may be embodied otherwise without departing from such principles.

LIST OF REFERENCE NUMBERS 100, 200, 300 Ventilator
101 Housing
102 Patient
104, 204, 304 Tube system
106, 306 Exhalation tube
107 Ventilation circuit
109 Y-piece
110, 210, 310, 310' Sensor element
112, 312, 312' Measured variable
114 Interface for the sensor element
117 Blower or similar device
120, 220, 320 Inhalation valve or exhalation valve
122, 322 Mount
130, 230, 330 Control unit
132 Valve cable
140 Predefined area
150, 250 Patient interface
207 Breathing gas flow
208, 308 Inhalation tube
260, 360 Calibration information
270 Output unit
272 Display
305 Ventilation system
362 Predefined tube resistance
400 Process
410, 420, 430, 440 Process steps

What is claimed is:

1. A ventilator for ventilating a patient by a high-flow oxygen therapy via a tube system providing at least a portion of a ventilation circuit of the ventilator, the ventilator comprising:
a sensor device comprising at least one sensor element, the sensor device being arranged and configured to determine and to output a measured variable within the tube system, wherein the measured variable indicates a gas flow within the tube system;
an actuatable valve configuration comprising at least one of an actuatable inhalation valve or an actuatable exhalation valve, the actuatable valve configuration being arranged and configured to make possible a flow of a breathing gas out of the ventilation circuit of the ventilator;
a control unit configured to regulate a ventilation pressure provided by the ventilator via the sensor device and the actuatable valve configuration such that a predefined maximum pressure is not exceeded in a predefined area of the tube system; and
a blower, wherein the control unit carries out the regulation of the ventilation pressure exclusively via the actuatable valve configuration without changing a blower output of the blower.

2. The ventilator in accordance with claim 1, wherein the ventilator is configured to keep the actuatable valve configuration closed if the predefined maximum pressure is not reached in the predefined area of the tube system.

3. The ventilator in accordance with claim 1, wherein the at least one sensor element is arranged within an exhalation tube of the tube system.

4. The ventilator in accordance with claim 1, wherein the actuatable valve configuration further comprises at least one of an electrically actuatable inhalation valve or an electrically actuatable exhalation valve.

5. The ventilator in accordance with claim 1, wherein the sensor device comprises a pressure sensor or a flow sensor or both a pressure sensor and a flow sensor.

6. The ventilator in accordance with claim 1, wherein the control unit is further configured to regulate the ventilation pressure provided based on calibration information.

7. The ventilator in accordance with claim 6, wherein the calibration information indicates a relationship between the pressure present in the predefined area of the tube system and the gas flow measured by the sensor device.

8. The ventilator in accordance with claim 6, wherein the calibration information is based on a tube resistance of the tube system.

9. The ventilator in accordance with claim 1, wherein the predefined area of the tube system is an end of an inhalation tube or an exhalation tube, wherein the end of the inhalation tube or the exhalation tube points towards or is adjacent to a patient being ventilated or to be ventilated.

10. The ventilator in accordance with claim 1, further comprising a ventilator housing, wherein the actuatable valve configuration is arranged together with the control unit in the ventilator housing.

11. The ventilator in accordance with claim 1, wherein the at least one of the actuatable inhalation valve or the actuatable exhalation valve has only two states comprising an open valve position and a closed valve position.

12. A ventilation system for ventilating a patient by a high-flow oxygen therapy, the ventilation system comprising:
a tube system comprising an inhalation tube and an exhalation tube;
a ventilator comprising:
a sensor device comprising at least one sensor element, the sensor device being arranged and configured to determine and to output a measured variable within the tube system, wherein the measured variable indicates a gas flow within the tube system;
an actuatable valve configuration comprising at least one of an inhalation valve or an exhalation valve, the actuatable valve configuration being arranged and configured to make possible a flow of a breathing gas out of a ventilation circuit of the ventilator;
a control unit configured to regulate a ventilation pressure provided by the ventilator via the sensor device and the actuatable valve configuration such that a predefined maximum pressure is not exceeded in a predefined area of the tube system, wherein the tube system is connected to the ventilator for providing the ventilation circuit; and a blower, wherein the control unit carries out the regulation of the ventilation pressure exclusively via the actuatable valve configuration without changing a blower output of the blower.

13. The ventilation system in accordance with claim 12, wherein the tube system is configured to be connected to the patient by means of nasal prongs.

14. The ventilation system in accordance with claim 12, wherein the ventilator is configured to keep the actuatable valve configuration closed if the predefined maximum pressure is not reached in the predefined area of the tube system.

15. The ventilation system in accordance with claim 12, wherein the at least one sensor element is arranged within the exhalation tube of the tube system.

16. The ventilation system in accordance with claim 12, wherein:

the actuatable valve configuration further comprises at least one of an electrically actuatable inhalation valve or an electrically actuatable exhalation valve; and the sensor device comprises a pressure sensor or a flow sensor or both a pressure sensor and a flow sensor.

17. A process for regulating a ventilation pressure provided by a ventilator during a high-flow oxygen therapy via a tube system, the process comprising the steps of:

providing an actuatable valve configuration comprising at least one actuatable inhalation valve or actuatable exhalation valve for making possible a flow of a breathing gas of a ventilation circuit of the ventilator, the ventilator comprising a blower;

determining and outputting a measured variable within the tube system, wherein the measured variable indicates a gas flow within the tube system; and regulating a ventilation pressure provided by the ventilator via a control unit controlling the at least one actuatable valve configuration such that a predefined maximum pressure is not exceeded in a predefined area of the tube system, wherein the ventilation pressure is regulated exclusively via the control unit controlling the actuatable valve configuration without changing a blower output of the blower.

18. The process according to claim 17, wherein a computer program with a program code carries out at least one or more of determining and outputting a measured variable and regulating the ventilation pressure with the program code being executed on a computer, on a processor or on a programmable hardware component.

* * * * *